United States Patent [19]

Miksovsky et al.

[11] 4,025,503
[45] May 24, 1977

[54] MANUFACTURE OF AZIRIDINECARBOXYLIC ACID ESTERS

[75] Inventors: Felix Miksovsky; Rolf Fikentscher, both of Ludwigshafen, Germany

[73] Assignee: BASF Aktiengesellschaft, Ludwigshafen, Germany

[22] Filed: July 5, 1974

[21] Appl. No.: 486,216

[30] Foreign Application Priority Data

July 7, 1973  Germany .......................... 2334656

[52] U.S. Cl. .......................................... 260/239 E
[51] Int. Cl.$^2$ ...................................... C07D 203/18
[58] Field of Search ...................... 260/239 E, 491

[56] References Cited

UNITED STATES PATENTS 2,089,127   8/1937   Lock .................................. 260/491

OTHER PUBLICATIONS

Tsou et al., J. Medl. Chem. 6, 435–439 (1963).
Eckert et al., cited in Theilheimer, vol. 21, No. 261 (1966).

*Primary Examiner*—Donald G. Daus
*Assistant Examiner*—Mark L. Bach
*Attorney, Agent, or Firm*—Keil, Thompson & Shurtleff

[57] ABSTRACT

Aziridinecarboxylic acid esters are prepared by transesterification of aziridinecarboxylic acid methyl, ethyl or propyl esters in the presence of a high-boiling paraffin hydrocarbon and optionally of an amine.

10 Claims, No Drawings

MANUFACTURE OF AZIRIDINECARBOXYLIC ACID ESTERS

This application discloses and claims subject matter described in German patent application P 23 34 656.7, filed July 7, 1953, which is incorporated herein by reference.

The invention relates to an improved process for the manufacture of aziridinecarboxylic acid esters of the general formula

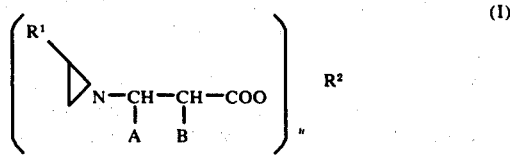

in which A is hydrogen or the grouping $(\text{-COO})nR^2$, B is hydrogen or methyl, $R^1$ is hydrogen or short-chain alkyl, for example alkyl of 1 to 5 carbon atoms, and $R^2$ is the n-valent radical of an n-valent alcohol of 2 or more carbon atoms, and $n$ is an integer which is at least 1 and is preferably 2 to 5 and especially 2.

The process to which the improvement relates is the reaction of compounds of the general formula (I), wherein $R^2$ is a radical of methyl alcohol, ethyl alcohol or propyl alcohol, with any other compound which carries one or more alcoholic OH groups, in the presence of a basic transesterification catalyst, and with removal of methyl alcohol, ethyl alcohol or propyl alcohol, from the esterification equilibrium, by distillation.

As can be seen, the compounds (I) embrace esters of the following acids substituted in the 3-position by an aziridine (= ethyleneimino) radical: propionic acid, isobutyric acid, succinic acid and optionally 2-methylsuccinic acid.

If $n$ is greater than 1, especially 2, and A is the abovementioned grouping $(\text{-COO})nR^2$, the compounds (I) can, accordingly, be polymeric ethyleniminosuccinic acid esters which can be represented by the more detailed formula (II):

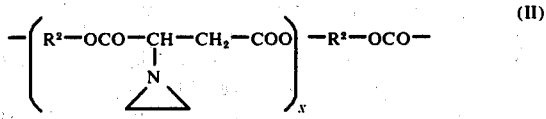

where X is the degree of polymerization which can assume values of, for example, from 5 to 5,000.

Aziridinecarboxylic acid esters can be manufactured by esterifying α-unsaturated carboxylic acids, such as acrylic acid, methacrylic acid and crotonic acid, with a suitable alcohol, and adding ethyleneimine to the double bond of the ester; this is described, for example, in U.S. Pat. No. 2,596,200 and German Laid-Open Specification No. 1,745,810. According to a publication by R. Huttel in "Fette, Seifen, Anstrichmittel", volume 64, pages 107 to 110 (1962), the same reaction has also already been investigated in the case of unsaturated polyesters, where it gives polyethyleniminopolyesters which are suitable for use as, for example, raw materials for coatings, or plastics or textile finishes.

This simple conventional method suffers from the following disadvantages, inter alia: in spite of cautious acid catalysis (with sulfuric acid), and even if the reaction is carried out in the presence of stabilizers, such as, for example, phenothiazine or hydroquinone, and using a low-boiling entrainer, the undesirable polymerization occurring at the double bond can in many cases not be prevented entirely. The removal or neutralization of the added acid, which is known to be absolutely essential before the produce is reacted with alkyleneimines, can only be achieved with difficulties which ultimately manifest themselves, in most cases, in poor shelf life of the end products.

A substantially better method of manufacture of such aziridine-carboxylic acid esters is via the trans-esterification reaction of the relatively easily obtainable methyl, ethyl or propyl ester with a corresponding alcohol, along the lines of the following equation:

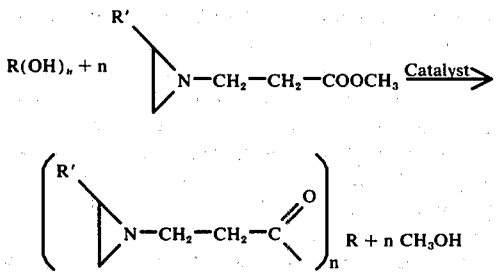

In this equation, $R^1$ is hydrogen or lower alkyl of, for example, 1 to 4 carbon atoms and $n$ is an integer.

This trans-esterification process for aziridinepropionic acid esters is described in principle in French Pat. No. 1,544,210. However, if the trans-esterification is carried out by the method described in this patent, the desired aziridinepropionic acid esters can only be obtained in a very impure form and in very poor yield. The process fails particularly when seeking to manufacture esters of alcohols of higher molecular weight or seeking to manufacture polymeric esters.

Whilst attempts have been made to displace the equilibrium reaction in favor of the desired ester by distilling off the methanol liberated, experience has shown that this can only be achieved incompletely; alcohols of higher molecular weights, in particular, retain the voltaile methanol tenaciously and the result is incomplete conversion.

In addition, the high temperatures which — according to the details given in the French patent specification — are required even when using lower alcohols, that is to say temperatures from 150° to 170° C, frequently destroy at least a part of the reaction product and a considerable portion of the aziridinocarboxylic acid methyl ester distils with the methanol.

The result is that the known process requires a large excess of methyl ester, which is removed at the end of the reaction. Apart from the fact that the use of a large excess of the relatively expensive methyl ester is uneconomical, the quantitative removal of this ester from reaction products which at times are very viscous (and are frequently solid at room temperature) presents great difficulties. However, for toxicological reasons it is necessary to remove the aziridinecarboxylic acid methyl ester quantitatively from the products.

We have now found that a process of the abovementioned type can be carried out better than hitherto, and with certain advantages, if the reason is carried out in the presence of a paraffin hydrocarbon of 7 to 12 carbon atoms and methyl alcohol, ethyl alcohol or propyl alcohol is distilled off with the paraffin hydrocarbon.

Paraffin hydrocarbons for the purposes of the invention are to be understood as straight or branched members of the series from heptane to dodecane. n-Octane, isoctane, nonanes and n-decane, which have favorable boiling points and are readily obtainable, are preferred; to some extent, technical mixtures of these substances can also be used, provided they do not contain any objectionable impurities. One of the advantages is that the lower alcohol may be distilled under gentle conditions even from viscous reaction mixtures.

The process according to the invention can in many cases be carried out with further advantage by using a tertiary amine, or the actual aziridinecarboxylic acid ester present, as a trans-esterification catalyst. This peculiarity also appears to be novel, though, of course, the known trans-esterification catalysts, for example alkali metal alcoholates, quaternary ammonium bases and others, are also suitable. It is particularly advantageous to use tertiary amines (for example tri-n-butylamine, N-dimethyl-N-cyclohexylamine, di-aza-1,4-bicyclo-[2,2,2]-octane (dabco), dimethyl-palm kernel fatty amine or diisopropylethylamine) if the alcohol to be converted contains primary OH groups, generally at least one equivalent per 500 equivalent weight units; the amine should have a sufficiently high boiling point that it does not distil with the paraffin hydrocarbon/alcohol and should be liquid, at least at room temperature. The use of such liquid tertiary amines at trans-esterification catalysts offers considerable advantages over the use of alkali metal alcoholates. These include the fact that homogeneous catalysis is concerned in every case, that the small amounts of tertiary amine in most cases do not interfere and can be left in the product, and that the involved removal of the catalyst by filtering the hot reaction mixture is dispensed with. In addition, the color of the product obtained is better in many cases.

The paraffin hydrocarbons according to the invention are all able to form azeotropes with methanol, ethanol or propanol (n-octane/methanol: 63° C, containing 72% of methanol; n-decane/methanol: 65°, containing 92% of methanol); whilst the cited French patent contains a proposal that the reaction should be carried out at a high temperature and in the presence of a solvent which forms azeotropes of low boiling point, the presentation of the object of the invention, which is worded in very general terms (see page 7, bottom of left-hand column of the cited specification) contains no indication of the solution of the problem, all the more so since it is necessary that the presence of the desired solvent should ensure a high concentration of the alcohol to be converted (a polyol is mentioned by way of example). The element of surprise in the process according to the invention is that on addition of the paraffin hydrocarbons according to the invention, phase separation occurs in most cases, and in accordance with expectations, that is to say there is no "solvent" present at all; nevertheless it appears to be precisely this state of affairs which is responsible, or partly responsible, for the advantages of the invention.

The following general comments should be made on how to carry out the process according to the invention: trans-esterification reactions are known to be equilibrium reactions; it is therefore necessary to remove the alcohol, which is to be obtained from the ester, from the reaction mixture, and this is done, according to the invention, by distillation. Advantageously, the distillate, on again becoming liquid, separates into two layers. The lower layer obtained is the alcohol, and in the case of methanol and octane the methanol contains 20% of octane; the upper layer obtained is practically pure paraffin hydrocarbon which can be returned to the reaction. It is simple to follow the reaction by observing the amount of alcohol distilled off.

Recycling ensures that there is little consumption of paraffin hydrocarbon; the amount present in the process cycle or in the reaction can be, for example, 5 to 80%, based on the reactants, and there is no theoretical limit, at least no upper limit.

When using a tertiary amine as the trans-esterification catalyst, the latter should be a tertiary amine which is as high-boiling as possible to prevent it from being removed together with the alcohol distilled off.

If alkali metal alcoholates are used as the trans-esterification catalyst, monoalcohols and polyalcohols, containing primary or secondary OH groups, can be converted practically quantitatively to the corresponding aziridinoester. The alcoholate should be added in as finely divided a form as possible. The use of a paraffin hydrocarbon as a reaction promotor in many cases produces a lower viscosity of the reaction mixture and thus facilitates fine distribution of the catalyst in the reaction mixture.

The process according to the invention is carried out in the substantial absence of water; however, small amounts of water in general do not interfere, particularly if an alcoholate which takes up small amounts of water is used as the catalyst. The amount of the trans-esterification catalyst to be used is generally not critical. If amines or quaternary ammonium compounds are used, amounts from 0.05 to 3%, preferably from 0.1 to 2% (based on the amount of the reaction mixture) in general suffice. When using solid alkali metal alcoholates, it is difficult to specify a lower and upper limit to the suitable amount, since with a solid catalysis it is to be expected that the reaction rate will increase with the amount of alcoholate or with its effective surface area. The upper limit is in general determined less by chemical factors than by technological factors.

It is a substantial advantage of the process according to the invention that even when using very high molecular weight alcohols or polyhydric alcohols together with succinic acid esters, evidently leading to polymers, high reaction temperatures are no longer required; in general, the reaction is carried out at atmospheric pressure and at temperatures from 100° to 140° C, especially from 120° to 140° C. A slight increase or decrease in pressure is immaterial as long as it does not cause the azeotropes described to disappear. n-Octane has proved to be the best additive.

The process can be applied, for example, to the following compounds, or categories of compounds, containing OH groups: aliphatic, monohydric and polyhydric alcohols, such as, for example, octyl alcohol, ethylene glycol, diglycol, triglycol, diglycol monomethyl ether, butanediol, hexanediol, decanediol, trimethylolpropane, glycerol, pentaerythritol, sorbitol, polyethylene glycol ethers, polypropylene glycol ethers, polytetrahydrofuran, copolymers and block polymers of ethylene oxide, propylene oxide and tetrahydrofuran, stearyl alcohol and the like; oxalkylated alcohols, for example products of the reaction of the abovementioned alcohols with ethylene oxide and/or propylene oxide;

oxyalkylated amines, that is to say products of the reaction of primary and secondary amines with ethylene oxide and/or propylene oxide, such as ethylethanolamine or diisopropanolamine, and other reaction products of, for example, the following amines: ethylenediamine, diethylenetriamine and dipropylenetriamin, polyethyleneimine, polyamidoamines, stearylamine, n,q-dioxadodecylenediamine and the like; oligomers or polymers containing optional OH groups, such as polyesters (with free OH groups), for example polyesters obtained from trimethylolpropane and adipic acid, polyurethanes and the like; and natural substances, such as cellulose, starch, sugars and their reaction products which contain free OH groups.

Methanol is the preferred alcohol component of the aziridinocarboxylic acid ester employed as the starting product for the transesterification reaction. (its advantages are a low boiling point, low molecular weight and low cost, and above all the fact that it forms an azeotrope of both favorable composition and favorable boiling point with hydrocarbons such as octane and decane.)

However, in principle, ethanol or some other low-boiling alcohol can also be used provided it forms an zeotrope, of boiling point below the reaction temperature, with a paraffin hydrocarbon used according to the invention.

As has already been mentioned above, the reaction of aziridinosuccinic acid methyl ester with a polyhydric alcohol produces polyesters which are substituted by the reactive ethyleneimino group, in a polymer-analogous manner. The process of the invention can be applied with particular advantage to the manufacture of such polyethyleneiminopolyesters, since the method of preparation described by Huttel, loc.cit., is a polymer-homologous reaction attended by the difficulties generally known to occur with polymer-homologous reactions. Above all, unreacted monomeric ethyleneimine must be removed quantitatively — for toxocological reasons — from the polyester produced, and this problem can in practice only be solved with difficulty, if at all. In contrast, the manufacture of these polyesters by a trans-esterification reaction of previously formed ethylneimino derivatives not only takes place smoothly but also does not require monomeric ethyleneimine and is therefore currently the only genuinely feasible industrial method for the manufacture of polymers containing the aziridine ring, of the type mentioned, which have a good shelf life.

Coupled with the possibility of using, as the transesterification catalysts, small amounts of tertiary amines which in general do not interfere with the envisaged use of the polyethyleneiminopolyestes (which esters are used, for example, as raw materials for coatings), the invention thus provides the art with an outstandingly suitable and versatile process.

The amounts mentioned in the Examples which follow are by weight, if not specified; the designations used for polymeric glycols ($P_9$ and the like) indicate the average degree of polymerization or average molecular weight and are designations customary in the art.

EXAMPLE 1

180 parts of butanediol, 543 parts of $\beta$-aziridinopropionic acid methyl ester and 10 parts of dimethyl-palm kernel fatty amine in 400 parts of octane are heated in a nitrogen atmosphere. 160 parts of the methanol phase distil off in the course of approx. 11 hours at a bottoms temperature of 118° to 134° C. The azeotrope is distilled off through a small column.

The octane is distilled in vacuo from the reaction solution. This leaves butanediol di-[$\beta$-(aziridino)-propionic acid ester] in almost quantitative yield (565 g), in the form of a yellow liquid.

Aziridine-N: calculated 9.84.
found 9.5.
NMR: ($CDCl_3$).

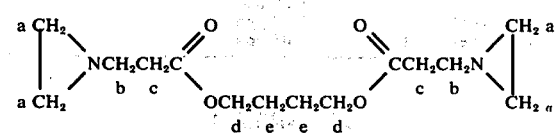

Triplet at 1.15 ppm $a$
Multiplet at 1.65 ppm $a, e$
Triplet at 2.49 ppm $b, c$
Triplet at 4.1 ppm $d$

EXAMPLE 2

414 parts of polyethylene glycol ether P9, 310 parts of aziridinopropionic acid ester, 145 parts of octane and 15 parts of dabco are heated whilst stirring in a nitrogen atmosphere. The methanol formed in the reaction distils off as an azeotrope, at a bottoms temperature of 121° to 131° C. The trans-esterification reaction is complete after approx. 7 hours. 83 parts of methanol distillate are obtained. After distilling off the octane in vacuo, a residue of 621 parts of polyethylene glycol ether P9 di-[$\beta$-(aziridino)-propionic acid ester] remains, in the form of a yellow liquid.
Analysis: Aziridine-N: found 4.4.
calculated 4.61.
NMR: ($CDCl_3$).

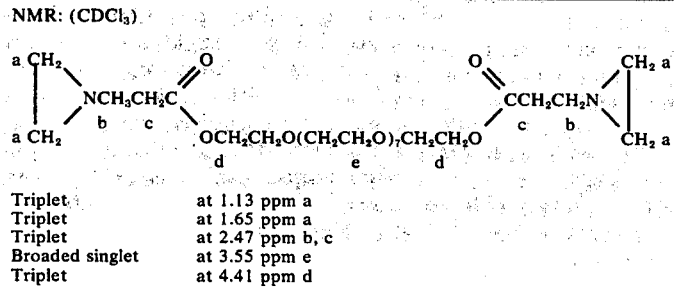

| Triplet | at 1.13 ppm a |
|---|---|
| Triplet | at 1.65 ppm a |
| Triplet | at 2.47 ppm b, c |
| Broaded singlet | at 3.55 ppm e |
| Triplet | at 4.41 ppm d |

EXAMPLE 3

178 parts of trimethylolpropane, 500 parts of octane, 516 parts of $\beta$-aziridinopropionic acid methyl ester and 40 parts of dimethylpalm kernel fatty amine are heated together in a nitrogen atmosphere, and stirred vigorously. The methanol formed in the reaction distils off azeotropically (boiling point 63° C) with octane, at a bottoms temperature of 124° to 128° C. 162 parts of methanol distillate are obtained in the course of approx. 6 hours. After distilling off the octane, the trimethylolpropane tris-[β-(aziridino)-propionic acid ester] remains, in practically quantitative yield, as a yellow liquid.

Analysis: Aziridine-N: found 9.5. calculated 9.88. (NMR: (CDCl₃).

NMR:(CDCl₃)

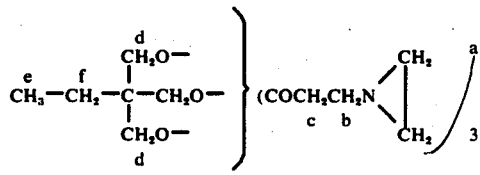

| Diffuse triplet | at approx. | 0.9 ppm e |
| Triplet | at | 1.15 ppm a |
| Triplet | at | 1.58 ppm a, f |
| Diffuse triplet | at | 2.48 ppm b, c |
| Diffuse triplet | at | 4.05 ppm d |

EXAMPLE 4

1,220 parts of an oxyethylated polypropylene glycol ether 2,000 (polypropylene oxide (PO) of molecular weight 2,000, which has been reacted with 10 moles of ethylene oxide (EO), 141 parts of β-aziridinipropionic acid methyl ester, 400 parts of octane and 10 parts of dimethyl-palm kernel fatty amine are heated, and stirred, in a nitrogen atmosphere. The methanol distils azeotropically with octane at a bottoms temperature of 126° to 135° C. After approx. 3 hours, the methanol distillate amounts to 40 parts. After distilling off the octane, 1,295 parts of di-[β-(aziridino)-propionic acid ester] of polypropylene glycol ether 2,000 + 10 EO are obtained as a light brown viscous liquid.

The product self-emulsions in water.

Analysis: Aziridine-N: found 0.97. calculated 1.06.

EXAMPLE 5

A solution of 414 parts of polyglycol ether P9 (a polyether consisting of ethylene oxide units), 284 parts of β-aziridinopropionic acid methyl ester, 145 parts of octane and 15 parts of tributylamine is heated at from 120° to 140° C. This causes the methanol to distil off azeotropically. After approx. 7 hours, the methanol distillate amounts to 82 parts. After distilling off the octane in vacuo, polyglycol ether P9 di- β-(aziridino)-propionic acid ester is obtained in practically quantitative yield (610 parts), in the form of a yellow liquid. A small proportion of the excess aziridinopropionic acid methyl ester is present in the methanol distillate whilst the bulk of the excess aziridinopropionic acid methyl ester distils off with the octane.

Analysis: Aziridine-N: calculated 4.61.
found 4.3.

EXAMPLE 6

1,096 parts of glycerol which has first been propoxylated and then ethoxylated (glycerol + 85 PO + 30 EO), 71 parts of β-aziridinopropionic acid methyl ester, 400 parts of octane and 5 parts of dimethyl-palm kernel fatty amine are heated under nitrogen and stirred vigorously. The methanol (18 parts) distils off in the course of 4 hours at temperatures from 122° to 137° C. After distilling off the octane in a high vacuum until the bottoms temperature reaches 80° C, the di[β-(aziridino)-propionic acid ester] of glycerol alkoxylated with 85 moles of PO and 15 moles of EO is obtained in quantitative yield, in the form of a pale yellow oily liquid. Analysis: Aziridine-N: calculated 0.61. found 0.57.

The product self-emulsifies in water.

EXAMPLE 7

750 parts of polytetrahydrofuran of molecular weight 1,000 are reacted with 660 parts of ethylene oxide in the presence of 7.5 parts of sodium methylate in an autoclave at 120° to 125° C. After distilling off volatiles in vacuo until the temperature reaches 100° C, 1,276 parts of oxyethylated polytetrahydrofuran 1,000 are obtained. This product is mixed with 193.5 parts of aziridinopropionic acid methyl ester and 400 parts of octane and the mixture is heated in a nitrogen atmosphere. The methanol/octance azeotrope distils off at a bottoms temperature of 119° to 145° C. After approx. 7 hours, 55 parts of methanol (containing approx. 20 per cent by weight of octane) are obtained. After distilling off the octane in a high vacuum, 1,425 parts of the diaziridinopropionic acid ester of oxyethylated polytetrahydrofuran 1,000 are obtained as a light brown viscous liquid.

Analysis: Aziridine-N: found 1.20.
calculated 1.25.

EXAMPLE 8

19,725 parts of polytetrahydrofuran (molecular weight: 2,000) and 2,675 parts of β-aziridinopropionic acid ester are dissolved in 4,340 parts of octane, 118 parts of finely powdered sodium methylate are added whilst stirring, and the mixture is heated. At approx. 123° C bottoms temperature, the methanol-octane azeotrope begins to distil off (top temperature 63° C). After approx, 12 hours, approx. 819 parts of the lower layer of distillate are obtained (containing approx. 20 per cent by weight of octane and approx. 5% of aziridinopropionic acid methyl ester).The reaction mixture is filtered whilst still hot (at approx. 70° C) through cotton canvas, and the octane and unreacted aziridinopropionic acid ester are distilled from the filtrate in vacuo (maximum bottoms temperature 90° C). Approx. 21,000 parts of polytetrahydrofuran 2,000 di[β-(aziridino)-propionic acid ester] remain in the form of a yellow viscous liquid. On prolonged standing at room temperature, the product solidifies to a light-colored waxy mass.

Analysis: Aziridine-N: found 1.16.
calculated 1.28.

NMR: (CDCl₃)

NMR:(CDCl₃)

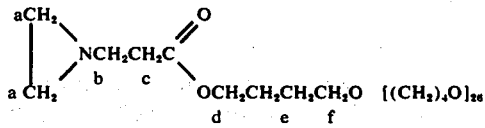

-continued $$\text{CH}_2\text{CH}_2\text{CH}_2\text{O} \underset{e}{\overset{}{\diagup}} \overset{\overset{O}{\diagdown\!\!\diagdown}}{\underset{d}{CCH_2CH_2N}} \underset{a}{\overset{\overset{a}{CH_2}}{\diagdown\!\!\diagup}} \overset{}{\underset{CH_2}{\big|}}$$

| Triplet | at 1.15 ppm a |
| Multiplet | at 1.65 ppm a, e |
| Diffuse triplet | at 2.58 ppm b, c |
| Multriplet | at 3.5 ppm f |
| Multriplet | at 4.25 ppm d |

EXAMPLE 9

234 parts of butanediol, 374 parts of aziridinosuccinic acid dimethyl ester, 350 parts of octane and 8 parts of dimethyl-palm kernel fatty amine are heated together in a nitrogen atmosphere and stirred. At 115° to 124° C bottoms temperature, the methanol formed by trans-esterification distils off. 136 parts of methanol layer are obtained in the course of approx. 6 hours.

After distilling off the octane in acuo, 487 parts of aziridinosuccinic acid butanediol polyester are obtained.

Analysis: Aziridine-N: found 5.1.
calculated 5.83.

The product is readily soluble at room temperature in isopropanol, acetone, tetrahydrofuran, methyl ethyl ketone and ethyl acetate.

EXAMPLE 10

534 parts of oxyethylated bisphenol A (bisphenol A + 2 EO), 234 parts of aziridinosuccinic acid dimethyl ester, 390 parts of octane and 9 parts of dimethyl-palm kernel fatty amine are heated in a nitrogen atmosphere and stirred vigorously. The methanol distils off azeotropically at a bottoms temperature of 114° to 124° C. 90 parts of methanol distillate are obtained in the course of approx. 4 ½ hours. After distilling off the octane in vacuo, 680 parts of aziridinosuccinic acid polyester of bis-ethoxy-bisphenol A are obtained. Melting range: approx. 39° to 41° C. Yellow powder.

Analysis: Aziridine-N: found 2.2.
calculated 2.62.

EXAMPLE 11

452 parts of decanediol, 374 parts of aziridinosuccinic acid dimethyl ester, 400 parts octane and 10 parts of dimethyl-palm kernel fatty amine are heated in a nitrogen atmosphere and stirred vigorously. The methanol (approx. 140 parts) formed in the reaction distils off in the course of approx. 7 hours at 125° to 131° C bottoms temperature. The octane is then distilled off in a high vacuum. 746 parts of aziridinosuccinic acid polyester (still containing traces of octane) remain, as a brown amorphous mass.

Analysis: Aziridine-N: found 3.86.
calculated 4.0

EXAMPLE 12

313 parts of decanediol, 241 parts of trimethylolpropane, 561 parts of aziridinosuccinic acid dimethyl ester, 400 parts of octane and 10 parts of dimethyl-palm kernel fatty amine are heated in a nitrogen atmosphere, and stirred vigorously. The methanol-octane azeotrope distils off at 122° to 137° C reaction temperature. 228 parts of methanol layer are obtained in the course of approx. 5 hours. The octane is then distilled off in vacuo. The aziridinosuccinic acid polyester is left in practically quantitative yield (950 parts).

Analysis: Aziridine-N: found 4.24.
calculated 4.45.

EXAMPLE 13

360 parts of butanediol, 107 parts of trimethylolpropane, 748 parts of aziridinosuccinic acid dimethyl ester, 400 parts of octane and 12 parts of dimethyl-palm kernel fatty amine are heated together in a nitrogen atmosphere and stirred vigorously. The methanol formed by the trans-esterification reaction (totalling 315 parts) distils off in the course of approx. 3 ½ hours at bottoms temperatures of 112° to 126° C. The octane is then distilled off in vacuo until the bottoms temperature reaches 70° C, thus leaving approx. 1,000 parts of the aziridinosuccinic acid polyester (which still contains small amounts of solvent) as a brown mass. It is advantageous to dissolve the product in a solvent (for example in methyl ethyl ketone).

Analysis: Aziridine-N: found approx. 5.0.
calculated 5.82.

EXAMPLE 14

592 parts of decanediol, 98.5 parts of adipic acid dimethyl ester, 424 parts of aziridinosuccinic acid dimethyl ester, 500 parts of octane and 10 parts of dimethyl-palm kernel fatty amine are heated in a nitrogen atmosphere, and stirred. The methanol distils off azeotropically at 106° to 139° C bottoms temperature. 173 parts of methanol layer are obtained in the course of approx. 8 hours. After distilling off the octane in vacuo, approx. 1,000 parts of the polyester remain; this product is soluble, at room temperature, in isopropanol, acetone, toluene, tetrahydrofuran, dioxane and ethyl acetate.

Analysis: Aziridine-N: found 3.2.
calculated 3.4.

We claim:

1. A process for the manufacture of compounds of the formula

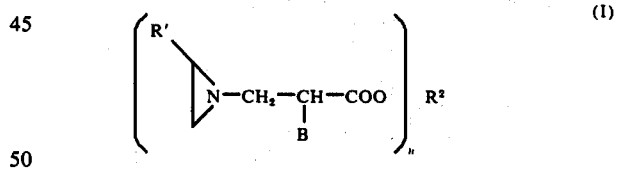

where B is hydrogen or methyl, R' is hydrogen or a $C_1$ to $C_5$ alkyl, $R^2$ is the n-valent radical of an n-valent primary alcohol other than methanol, ethanol or propanol and n is an integer of from 2 to 5 and is equal to the number of valences of the radical $R^2$, which comprises reacting a compound of formula I in which n is 1 and $R^2$ is methyl, ethyl or propyl with an n-valent primary alcohol other than methanol, ethanol or propanol, at a temperature of from 100° to 145° C in the presence of a basic transesterification catalyst and a paraffin hydrocarbon selected from the group consisting of n-octane, isooctane, a nonane, and n-decane with removal of methyl alcohol, ethyl alcohol or propyl alcohol from the esterification equilibrium by distillation.

2. A process as set forth in claim 1 wherein the transesterification catalyst is a tertiary amine which is liquid at room temperature and which has a sufficiently high boiling point that it does not distil with the parafin hydrocarbon/alcohol.

3. A process as set forth in claim 1 wherein the aziridine compounds of formula I are used as the transesterification catalyst.

4. A process as set forth in claim 1 wherein the paraffin hydrocarbon is n-octane.

5. A process as set forth in claim 1 wherein said reaction is carried out at a temperature of from 120° to 140° C and at atmospheric pressure.

6. A process for the manufacture of ethyleneiminosuccinic acid esters which comprises reacting a compound of the formula

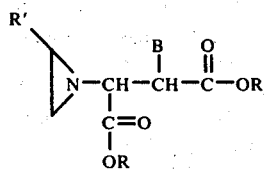

wherein B is hydrogen or methyl, $R^1$ is hydrogen or a $C_1$ to $C_5$ alkyl and R is methyl, ethyl or propyl, with an n-valent primary alcohol other than methanol, ethanol or propanol where n is an integer of from 2 to 5, at a temperature of from 100° to 145° C in the presence of a basic transesterificaion catalyst and a paraffin hydrocarbon selected from the group consisting of n-octane, isooctane, a nonane, and n-decane with removal of methyl alcohol, ethyl alcohol or propyl alcohol from the esterification equilibrium by distillation.

7. A process as set forth in claim 6 wherein the transesterification catalyst in a tertiary amine which is liquid at room temperature and which has a sufficiently high boiling point that it does not distil with the parafin hydrocarbon/alcohol.

8. A process as set forth in claim 6 wherein the paraffin hydrocarbon is n-octane.

9. A process as set forth in claim 6 wherein the reaction is carried out at a temperature of from 120 to 140° C and at atmospheric pressure.

10. A process as set forth in claim 1 wherein $n$ is 2.

* * * * *